(12) United States Patent
Auld (10) Patent No.: US 10,040,066 B2
(45) Date of Patent: Aug. 7, 2018

(54) APPARATUS FOR ANALYTE EXAMINATION

(71) Applicant: Advanced Technology Applications, LLC, Morgantown, WV (US)

(72) Inventor: Jeffery R. X. Auld, Raleigh, NC (US)

(73) Assignee: Advanced Technology Applications, LLC, Morgantown, WV (US)

(*) Notice: Subject to any disclaimer, the term of this patent is extended or adjusted under 35 U.S.C. 154(b) by 418 days.

(21) Appl. No.: 14/722,652

(22) Filed: May 27, 2015

(65) Prior Publication Data

US 2016/0303560 A1    Oct. 20, 2016

Related U.S. Application Data

(62) Division of application No. 14/688,331, filed on Apr. 16, 2015, now abandoned.

(51) Int. Cl.
*B01L 3/00* (2006.01)
*G01N 21/31* (2006.01)
*G01N 21/25* (2006.01)
*G01N 35/00* (2006.01)

(52) U.S. Cl.
CPC .......... *B01L 3/5027* (2013.01); *G01N 21/253* (2013.01); *G01N 21/31* (2013.01); *G01N 21/314* (2013.01); *G01N 35/00069* (2013.01); *B01L 2300/028* (2013.01); *B01L 2300/0803* (2013.01); *B01L 2300/16* (2013.01); *B01L 2300/168* (2013.01); *G01N 2201/061* (2013.01)

(58) Field of Classification Search
None
See application file for complete search history.

(56) References Cited

U.S. PATENT DOCUMENTS

2003/0096434 A1\* 5/2003 Krutzik ................ G01N 33/553
436/524

\* cited by examiner

*Primary Examiner* — Erik B Crawford
(74) *Attorney, Agent, or Firm* — McDonnell Boehnen Hulbert & Berghoff LLP (57) ABSTRACT

A biosensor disk includes a detection substrate with an upper side surface, a reflection substrate with a lower side surface facing oppositely toward the upper side surface, and fluidic channels reaching between the opposed side surfaces. The upper side surface has binding sites, and has non-binding sites adjoining the binding sites. The detection substrate is transparent at the non-binding sites. The lower side surface has non-reflective areas, and has reflective areas adjoining the non-reflective areas. The reflective areas are located opposite the non-binding sites and have discrete polygonal configurations of equal size and shape.

11 Claims, 7 Drawing Sheets

APPARATUS FOR ANALYTE EXAMINATION

RELATED APPLICATIONS

This application is a divisional of U.S. patent application Ser. No. 14/688,331, filed Apr. 16, 2015, entitled Method for Analyte Examination.

BACKGROUND

In the prior art, as shown for example in U.S. Pat. No. 8,735,846, a biosensor disk may have a spiral data path encoded with digital data. The data is established by a sequence of pits and lands on the surface of the disk. As the disk is rotated in a reading system, light from a laser or light emitting diode is directed onto the disk at the spiral data path. The system reads the encoded data as indicated by the light reflected from the pits and lands.

The disk further has detector chambers for containing analytes. Ligands are provided to bind specific analytes in place within the chambers. The detector chambers are interposed between the reader system and the spiral data path such that analytes in the chambers can obscure the transmission of light to and from the data path. Accordingly, alterations in the data read by the system indicate the presence of the specific analytes corresponding to the ligands in the chambers where the data path is obscured.

SUMMARY

An apparatus comprises a biosensor disk structure including a first substrate with a first inner surface, a second substrate with a second inner surface facing oppositely toward the first inner surface, and fluidic channels reaching between the first and second inner surfaces. The first inner surface has binding sites, and has non-binding sites adjoining the binding sites. The first substrate is transparent at the non-binding sites. The second inner surface has non-reflective areas, and has reflective areas adjoining the non-reflective areas. The reflective areas are located opposite the non-binding sites and have discrete polygonal configurations of equal size and shape.

In a preferred embodiment, the non-binding sites have discrete polygonal configurations that are sized and shaped equally with the reflective areas. The reflective areas are thus located coextensively opposite the non-binding sites.

Further regarding the preferred embodiment, the reflective and non-reflective areas are located in an assay region of the second inner surface, and the second inner surface further has a non-reflective spectral sensor discharge region circumferentially adjacent to the assay region.

DETAILED DESCRIPTION

The apparatus shown in the drawings has parts that are examples of the elements recited in the apparatus claims. These examples are described here to provide enablement and best mode without imposing limitations that are not recited in the claims.

Figure 1:
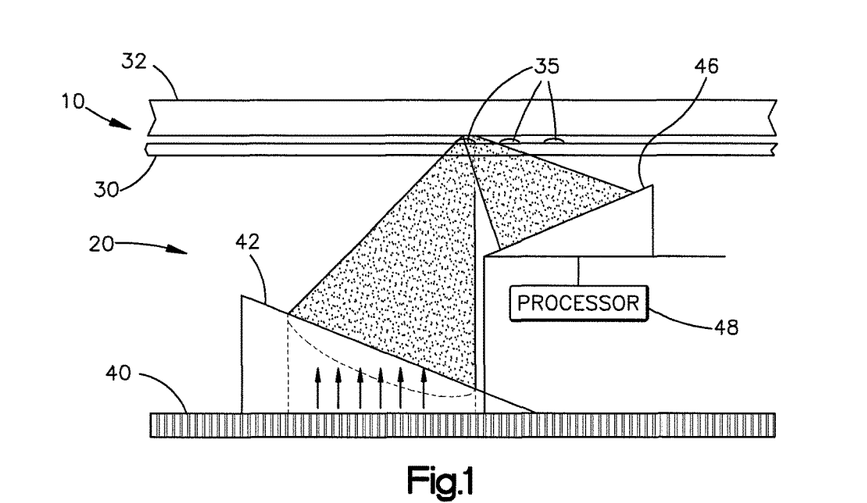
FIG. 1 is a schematic view of an apparatus including a biosensor disk and a system for examining a sample on the disk.

As shown schematically in FIG. 1, an apparatus includes a biosensor disk 10 and a system 20 for examining a sample on the disk 10. The parts of the disk 10 that are shown in FIG. 1 include a detection substrate 30 and a reflection substrate 32. Discrete units 35 of the sample, which contains biological or other analytes, are distributed within the disk 10 between the detection substrate 30 and the reflection substrate 32. The detection substrate 30 is transparent as needed for the sample units 35, when viewed from that side of the disk 10, to be visible on a background at the reflection substrate 32.

The parts of the system 20 in the example of FIG. 1 include a liquid crystal display (LCD) panel 40, a condenser lens 42, and a sensor array 46. In operation, the disk 10 rotates in its plane above the LCD panel 40. The LCD panel 40 emits light in a band of wavelengths. The condenser lens 42 condenses the emitted light into a spot of greater electromagnetic intensity comprised of the multiple wavelengths in the band, and directs it to the disk 10. Light reflected from the disk 10 reaches the sensor array 46.

As a sample unit 35 on the rotating disk 10 moves across the path of light shown in the drawing, a processor 48 forms one or more images of the sample unit 35 on the background of the reflection substrate 32. By considering parameters such as size, shape and position of the sample unit 35 relative to the background in the images, the processor 48 can correlate those parameters with corresponding parameters of a reference substance, and can thus determine a degree of identity between the sample unit 35 and the reference substance. By comparing images formed at differing wavelengths, the processor 48 can compare the spectral response of the sample unit 35 with a known spectral response of the reference substance at the differing wavelengths, and can thus determine a further degree of identity between the sample unit 35 and the reference substance.

Figure 2:
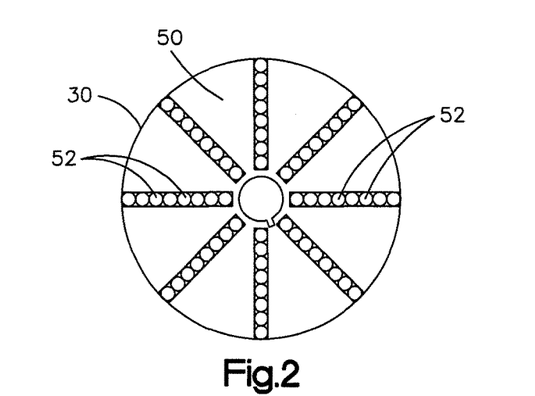
FIG. 2 is a side view of a part of the disk shown in FIG. 1.
Figure 3:
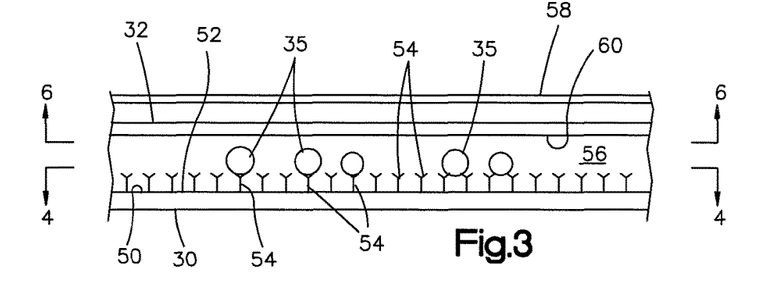
FIG. 3 is an exploded sectional view of parts of the disk of FIG. 1.

As shown separately in FIG. 2, the detection substrate 30 has an upper side surface 50 which, in the assembled disk 10 of FIG. 1, faces toward the reflection substrate 32. Rows of assay regions 52 extend radially across the upper side surface 50, and are equally spaced apart circumferentially around the upper side surface 50. Ligands 54 are provided at each assay region 52 to hold the sample units 35 in place between the two substrates 30 and 32, as shown in FIG. 3. Specifically, the ligands 54 selected for the imaging process are known to bind, accept or otherwise capture a specific reference substance that the process seeks to detect in the sample units 35. These and other features of the disk 10 can be provided as described in U.S. Pat. No. 8,735,846, which is incorporated by reference, including fluidic channels 56 for conveying the sample units 35 to the ligands 54, and a protective substrate 58.

Figure 4:
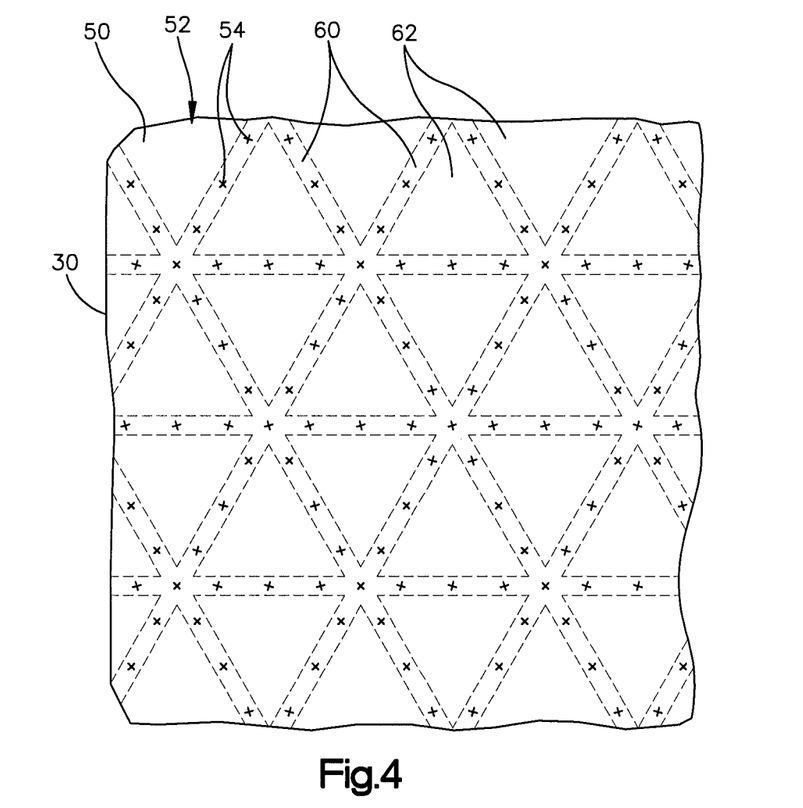
FIG. 4 is a view taken on line 4-4 of FIG. 3.

The ligands 54 at each assay region 52 are arranged to provide a pattern of binding and non-binding sites at the assay region 52. As shown partially in FIG. 4, the arrangement of ligands 54 in this particular example provides a uniformly repeating pattern of binding sites 60 shaped as narrow linear areas. The binding sites 60 delineate a corresponding pattern of non-binding sites 62 which, in the given example, are shaped as triangles with sides at the surrounding binding sites 60 and corners where the binding sites 60 intersect. The dimensions of the binding and non-binding sites 60 and 62 are known and stored as baseline data for the imaging process.

Figure 5:
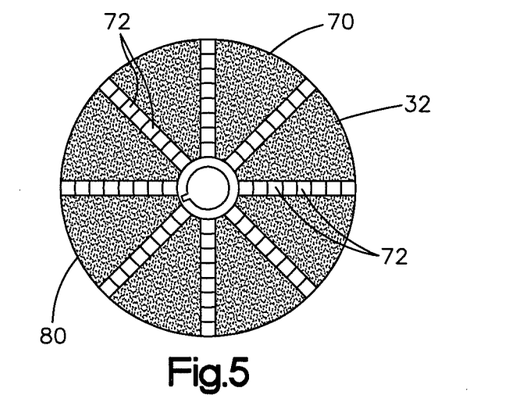
FIG. 5 is a side view of another part of the disk of FIG. 1.

As shown separately in FIG. 5, the reflection substrate 32 has a lower side surface 70 that faces the detection substrate 30. The lower side surface 70 also has rows of assay regions 72. Each assay region 72 on the reflection substrate 32 is located directly opposite an assay region 52 on the detection substrate 30. Moreover, each assay region 72 on the reflection substrate 32 has reflective surface areas 74 (FIG. 6) with the same triangular shape, size and pattern of arrangement as the non-binding sites 62 (FIG. 4) on the detection substrate 30. The reflective surface areas 74 are thus located coextensively opposite the non-binding sites 62. Each assay region 72 on the lower side surface 70 further has contiguous non-reflective surface areas 76 in an intersecting linear arrangement that matches and faces oppositely toward the linear binding sites 60 on the opposed assay region 52. Like the dimensions of the binding and non-binding sites 60 and 62, the corresponding dimensions of the reflective and non-reflective areas 74 and 76 are known and stored as baseline data for the imaging process.

Figure 6:
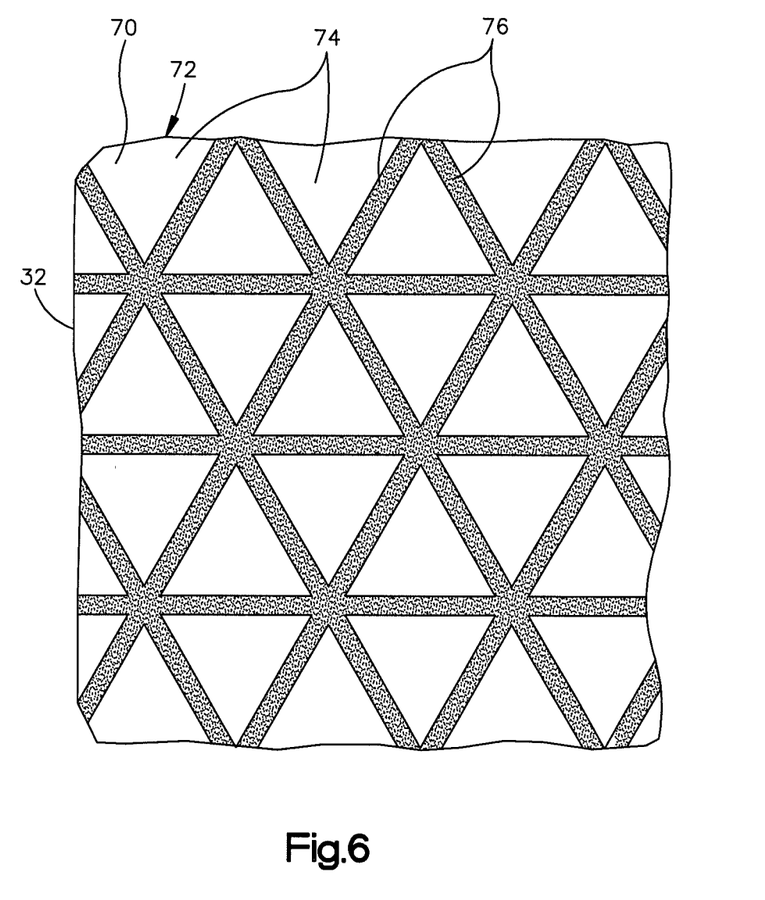
FIG. 6 is a view taken on line 6-6 of FIG. 3.

In operation, the system 20 performs the imaging process in a field of view having the reflection substrate 32 as a background, as noted above. This can begin with a baseline image of the reflection substrate 32 without any sample units 35, as shown in FIG. 6. Such a baseline image may serve as a reference for observing the position, size and/or shape of sample units 35 on the same background in other images.

Figure 7:
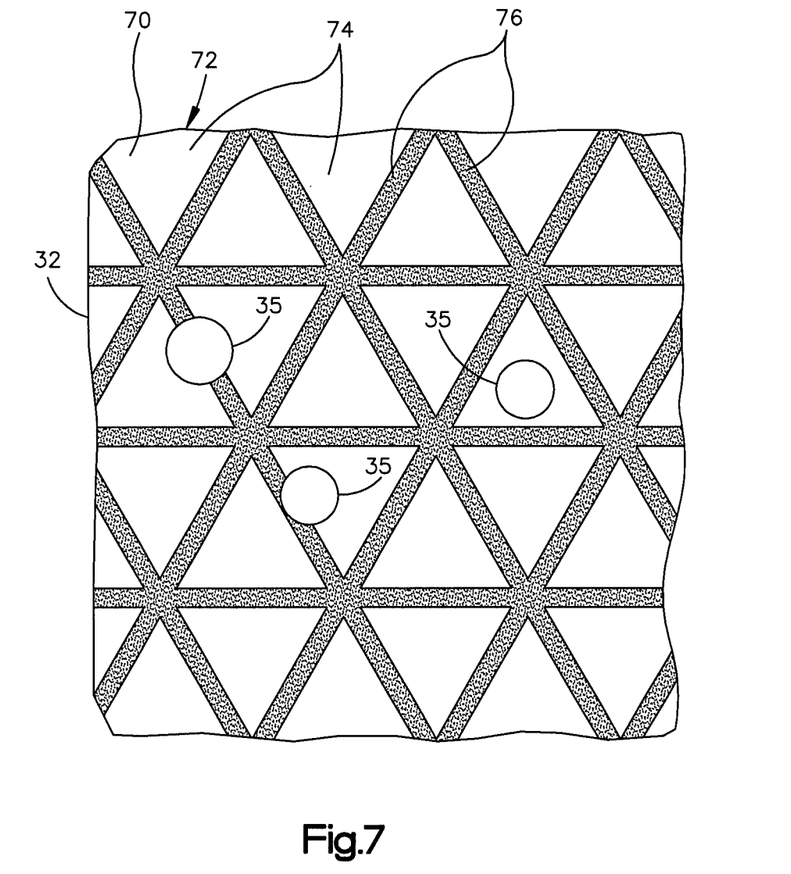
FIG. 7 is a view similar to FIG. 6 showing sample units for examination on the disk.
Figure 8:
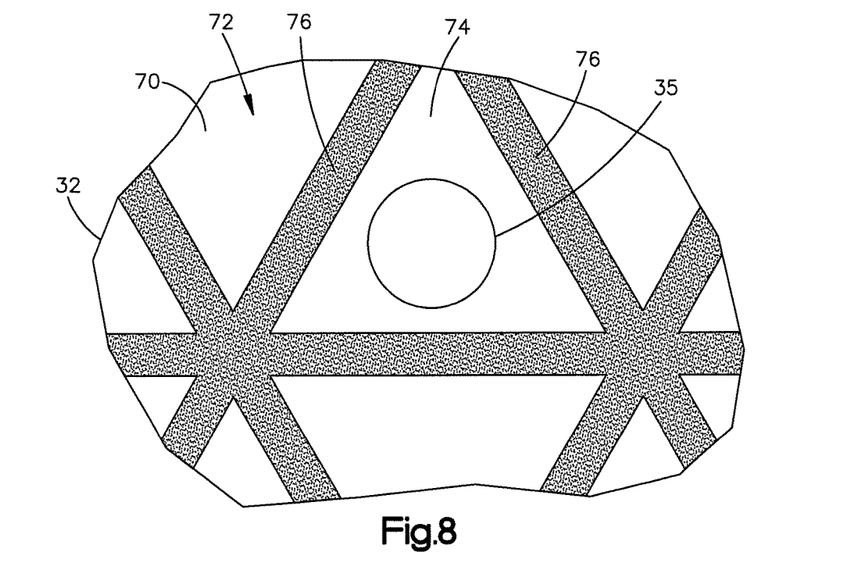
FIG. 8 is a view similar to FIG. 7 showing an image of a sample unit on the disk.
Figure 9:
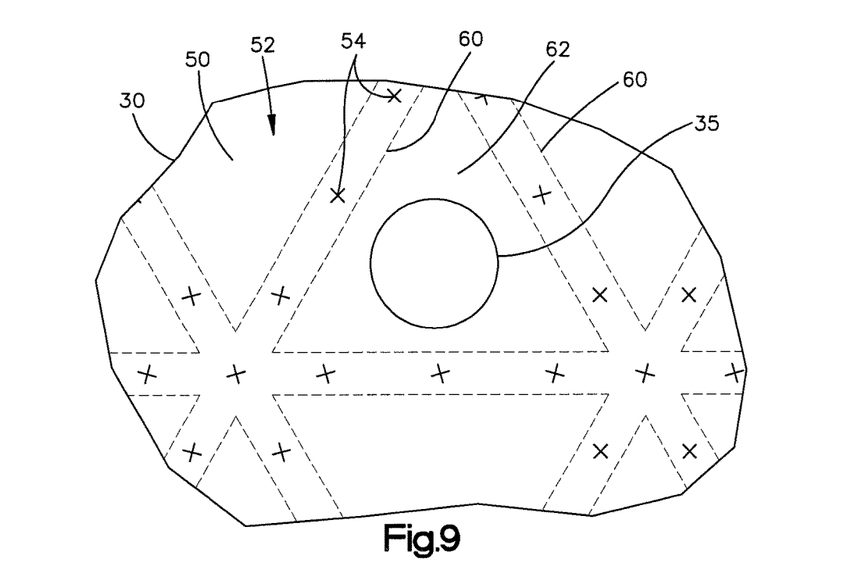
FIG. 9 is a view similar but opposite to the view of FIG. 8.

An image of the reflection substrate 32 with sample units 35 in the foreground may appear as shown partially in FIG. 7. As shown separately in FIG. 8, one such sample unit 35 is located entirely within a reflective surface area 74. That sample unit 35 is likewise located entirely within the coextensively opposed non-binding site 62 (FIG. 9). Since the sample unit 35 is shown to have reached that location without being bound by the ligands 54 on the detection substrate 30, its position strongly suggest the absence of the reference substance in this sample unit 35. If this unbound position of the sample unit 35 is taken as a threshold indication of distinction from the reference substance, the sample unit may be dismissed as lacking the reference substance.

Figure 10:
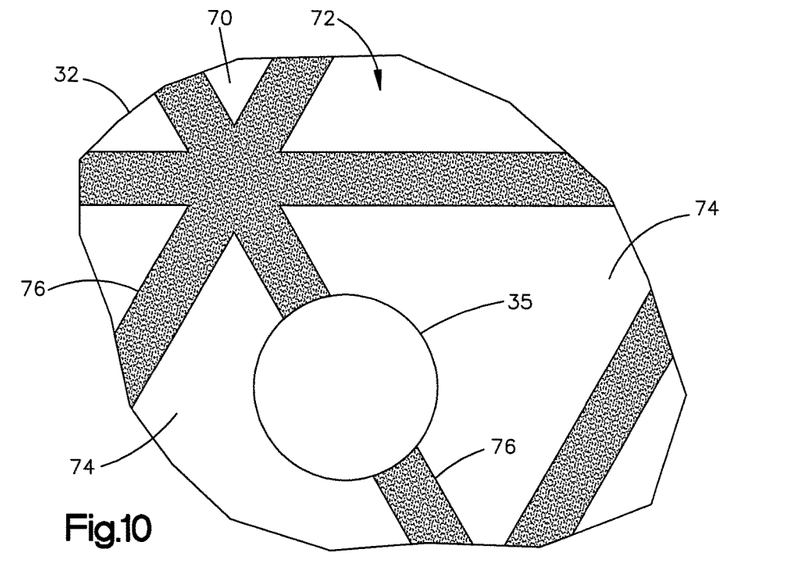
FIG. 10 is a view showing an image of another sample unit on the disk.
Figure 11:
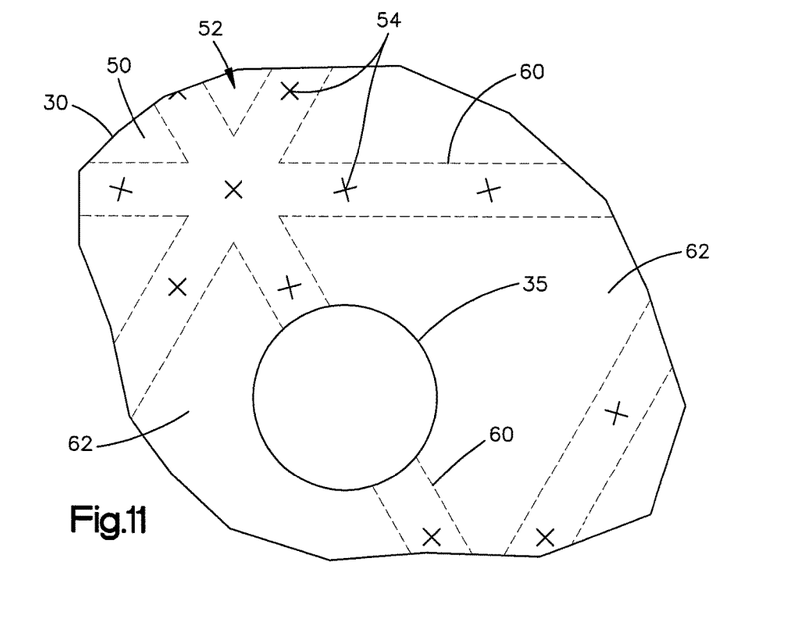
FIG. 11 is a view similar but opposite to the view of FIG. 10.

In the image shown partially in FIG. 10, a sample unit 35 is shown to overlie a non-reflective surface area 76 on the reflection substrate 32, and to reach across adjacent triangular reflective surface areas 74. This sample unit 35 is thus shown to be bound to the detection substrate 30 at the pattern of binding sites 60 provided by the ligands 54 (FIG. 11), and to reach onto adjacent triangular non-binding sites 62. Such binding of the sample unit 35 to the ligands 54 indicates the presence of the reference substance. Additionally, the shape of the sample unit 35 may be observed directly, and its size may be observed by comparison with the known dimensions of the reflective and non-reflective surface areas 74 and 76.

The degree of binding, the shape, and the size of the sample unit 35 can be compared with their known counterparts for the reference substance to assess the similarities or differences indicated for the sample unit 35 and the reference substance. If these comparisons satisfy threshold requirements of similarity, the sample unit 35 may be accepted as including the reference substance.

Figure 12:
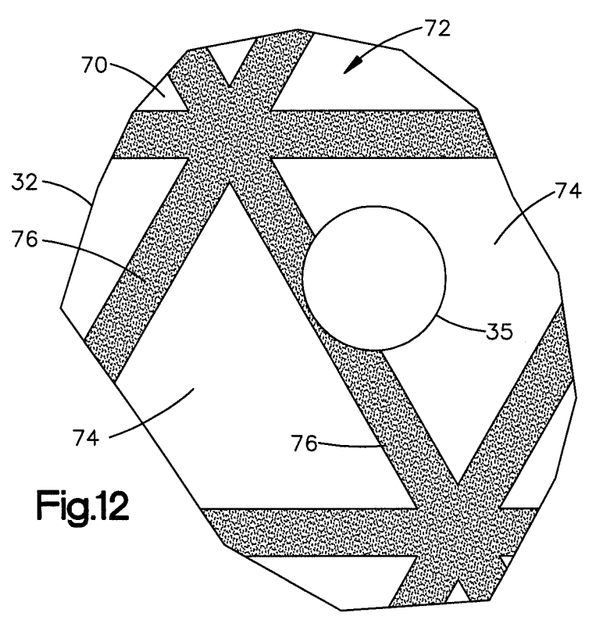
FIG. 12 is a view showing an image of yet another sample unit on the disk.

As an intermediate example, the image shown partially in FIG. 12 includes a sample unit 35 with a lesser degree of binding with the ligands 54, as compared with the example of FIG. 10. This is a lesser indication that the sample unit 35 includes the reference substance. The shape of the sample unit 35 is the same, but the different size provides a correspondingly different comparison with the reference substance. If these observations of bonding, shape and size are considered inconclusive, the imaging process may proceed with spectral response as a parameter.

Figure 13:
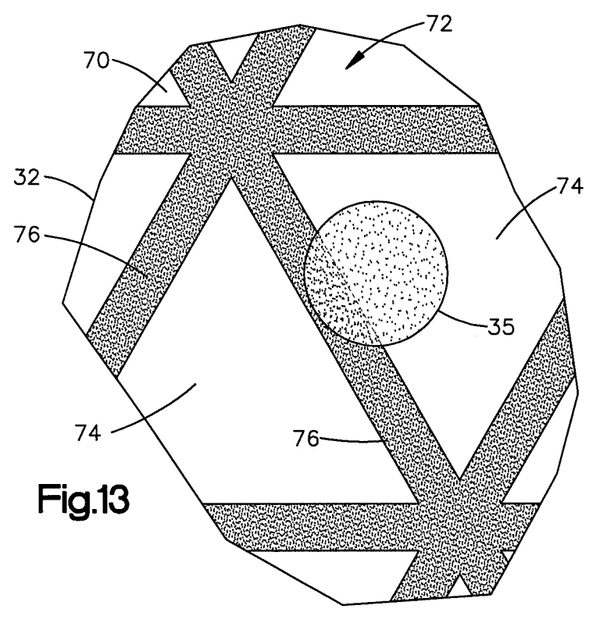
FIG. 13 is a view similar to FIG. 12 but shows an image formed with light of a differing wavelength.

Specifically, an image of the sample unit 35 is formed with light in a first band of wavelengths. In this example the image of FIG. 12 is taken as the image formed at the first band of wavelengths. The LCD panel 40 can then be operated to emit light in a second band of wavelengths different from the first, and another image is then formed with the light in the second band of wavelengths. This could be an image as shown in FIG. 13. A comparison of the images of FIGS. 12 and 13 shows that the sample unit 35 has greater reflectance and transmittance of light in the first band of wavelengths and greater absorption of light in the second band of wavelengths. This difference in spectral response of the sample unit is compared with a known difference in spectral response of the reference substance at the first and second bands of wavelengths. It is then determined whether or not the detected difference in spectral response meets a predetermined threshold of identity with the known difference.

In an alternative example, instead of using differing bands of wavelengths, light of only a single wavelength could be used for any one or more of the multiple exposures performed in a spectral response stage of the method, as long as multiple exposures differ in wavelength sufficiently to obtain a detectable difference in spectral response.

An additional feature of the disk 10 is shown in FIG. 5 where the lower side surface 70 of the reflection substrate 32 has non-reflective regions 80 reaching fully between the rows of assay regions 72. As a non-reflecting region 80 on the rotating disk 10 moves across the path of light shown in FIG. 1, it blocks the transmission of reflected light from the disk 10 to the sensor array 46. This enables the method to include an intervening discharging step between the formation of successive images by effectively exposing the sensor array 46 to darkness so that the sensor elements can fully drain the charges generated in one or more previous exposures to light reflected from the disk 10.

This written description sets for the best mode of carrying out the invention, and describes the invention so as to enable a person skilled in the art to make and use the invention, by presenting examples of elements recited in the claims. The patentable scope of the invention is defined by the claims, and may include other examples that occur to those skilled in the art. Such other examples, which may be available either before or after the application filing date, are intended to be within the scope of the claims if they have elements that do not differ from the literal language of the claims, or if they have equivalent elements with insubstantial differences from the literal language of the claims.

What is claimed is:

1. An apparatus comprising:
a biosensor disk structure including a first substrate with a first inner surface, a second substrate with a second inner surface facing oppositely toward the first inner surface, and fluidic channels reaching between the first and second inner surfaces;
wherein the first inner surface has binding sites that each include a ligand selected to capture a reference substance and non-binding sites that are substantially free of the ligand and that adjoin the binding sites, and the first substrate is transparent at the non-binding sites;
the second inner surface has non-reflective areas and reflective areas adjoining the non-reflective areas, the reflective areas are located opposite the non-binding sites, and the reflective areas have discrete polygonal configurations of equal size and shape.

2. The apparatus of claim 1 wherein the reflective areas are bounded by the non-reflective areas.

3. The apparatus of claim 1 wherein the non-reflective areas are contiguous around and between the reflective areas.

4. The apparatus of claim 1 wherein the non-binding sites are sized and shaped equally with the reflective areas such that the non-binding sites are located coextensively opposite the reflective areas.

5. The apparatus of claim 1 wherein the non-binding sites are bounded by the binding sites.

6. The apparatus of claim 1 wherein the binding sites are sized and shaped equally with the non-reflective areas such that the binding sites are located coextensively opposite the non-reflective areas.

7. The apparatus of claim 1 wherein the binding sites are contiguous around and between the non-binding sites.

8. The apparatus of claim 1 wherein the polygonal configurations are triangular.

9. The apparatus of claim 1 wherein the reflective and non-reflective areas are located in an assay region of the second inner surface, and the second inner surface further has a non-reflective spectral sensor discharge region circumferentially adjacent to the assay region.

10. The apparatus of claim 9 wherein the assay region of the second inner surface is one of plurality of assay regions that are alike and are arranged in rows extending radially across the biosensor disk structure, and the non-reflective spectral sensor discharge region is one of a plurality of regions of the second inner surface that are alike and are located circumferentially between adjacent rows of assay regions.

11. The apparatus of claim 10 wherein the non-reflective spectral sensor discharge regions of the second inner surface reach circumferentially fully between the adjacent rows of assay regions.

* * * * *